(12) United States Patent
Haverkost

(10) Patent No.: US 10,531,913 B2
(45) Date of Patent: *Jan. 14, 2020

(54) RF ELECTRODES ON MULTIPLE FLEXIBLE WIRES FOR RENAL NERVE ABLATION

(71) Applicant: Boston Scientific Scimed, Inc., Maple Grove, MN (US)

(72) Inventor: Patrick A. Haverkost, Brooklyn Center, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 538 days.

This patent is subject to a terminal disclaimer.

(21) Appl. No.: 15/204,490

(22) Filed: Jul. 7, 2016

(65) Prior Publication Data
US 2016/0317222 A1 Nov. 3, 2016

Related U.S. Application Data

(63) Continuation of application No. 13/184,677, filed on Jul. 18, 2011, now Pat. No. 9,408,661.
(Continued)

(51) Int. Cl.
*A61B 18/14* (2006.01)
*A61B 18/00* (2006.01)

(52) U.S. Cl.
CPC ............... *A61B 18/1492* (2013.01); *A61B 2018/00214* (2013.01); *A61B 2018/00226* (2013.01);
(Continued)

(58) Field of Classification Search
CPC ...... A61B 18/1492; A61B 2018/00214; A61B 2018/00226; A61B 2018/00232;
(Continued)

(56) References Cited

U.S. PATENT DOCUMENTS 5,772,590 A * 6/1998 Webster, Jr. ......... A61B 5/0422
600/374
2002/0165532 A1* 11/2002 Hill, III ............. A61B 18/1492
606/41

(Continued)

FOREIGN PATENT DOCUMENTS

EP 1009303 B1 7/2001
WO 9922659 A1 5/1999

*Primary Examiner* — Michael F Peffley
*Assistant Examiner* — Amanda L Zink

(57) ABSTRACT

A catheter includes a flexible shaft having a distal end dimensioned for deployment within a patient's renal artery. A number of elongated resilient members are mounted along a longitudinal length of the distal end of the shaft, and are extensible radially from the shaft at regions defined between longitudinally spaced-apart engagement locations. One or more electrodes are mounted on each of the resilient members at the radially extensible regions. A number of conductors are electrically coupled to the electrodes and extend along the shaft of the catheter. The elongated resilient members are collapsible when encompassed within a lumen of an outer sheath and extensible radially outward from the shaft at the regions defined between the longitudinally spaced-apart engagement locations when the catheter and the resilient members are axially extended beyond the distal tip of the sheath. RF energy is delivered to the electrodes for ablating perivascular renal nerves.

10 Claims, 12 Drawing Sheets

Related U.S. Application Data

(60) Provisional application No. 61/369,458, filed on Jul. 30, 2010, provisional application No. 61/418,667, filed on Dec. 1, 2010.

(52) U.S. Cl.
CPC ............... *A61B 2018/00232* (2013.01); *A61B 2018/00267* (2013.01); *A61B 2018/00434* (2013.01); *A61B 2018/00511* (2013.01); *A61B 2018/00577* (2013.01); *A61B 2018/1467* (2013.01); *A61B 2018/1475* (2013.01)

(58) Field of Classification Search
CPC .. A61B 2018/00511; A61B 2018/1475; A61B 2018/00577; A61B 2018/1467; A61B 2018/00434
See application file for complete search history.

(56) References Cited

U.S. PATENT DOCUMENTS

| | | | |
|---|---|---|---|
| 2003/0236455 A1 | 12/2003 | Swanson et al. | |
| 2006/0235286 A1* | 10/2006 | Stone ................. | A61B 5/02007 600/381 |
| 2011/0257523 A1* | 10/2011 | Hastings .............. | A61B 8/0891 600/439 |
| 2011/0264086 A1* | 10/2011 | Ingle ................. | A61B 18/1492 606/33 |

* cited by examiner

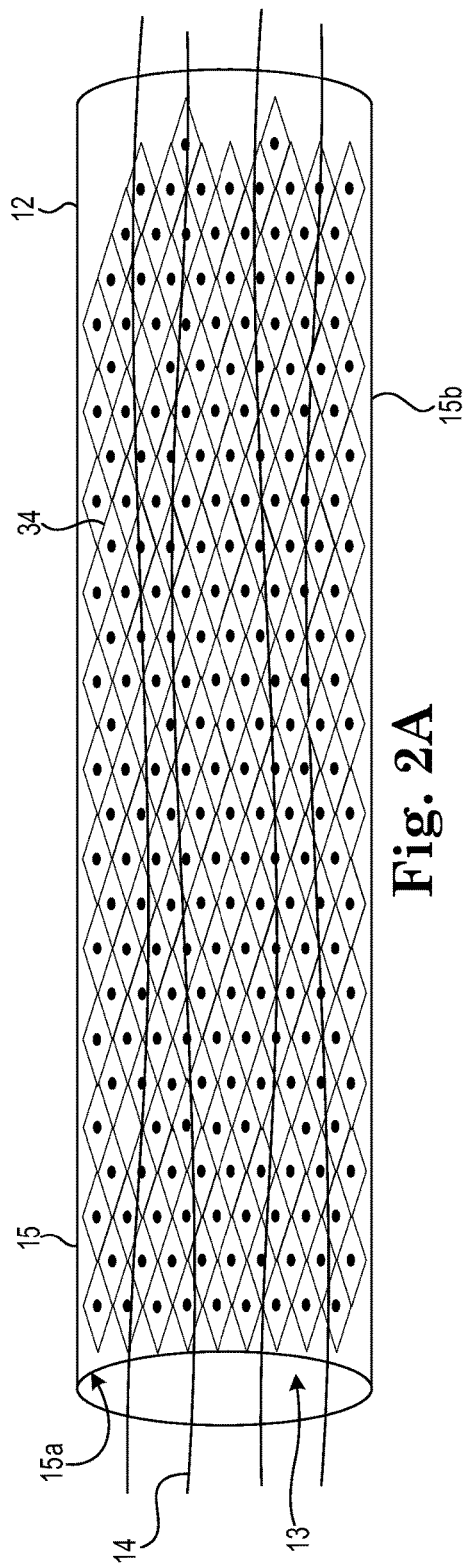
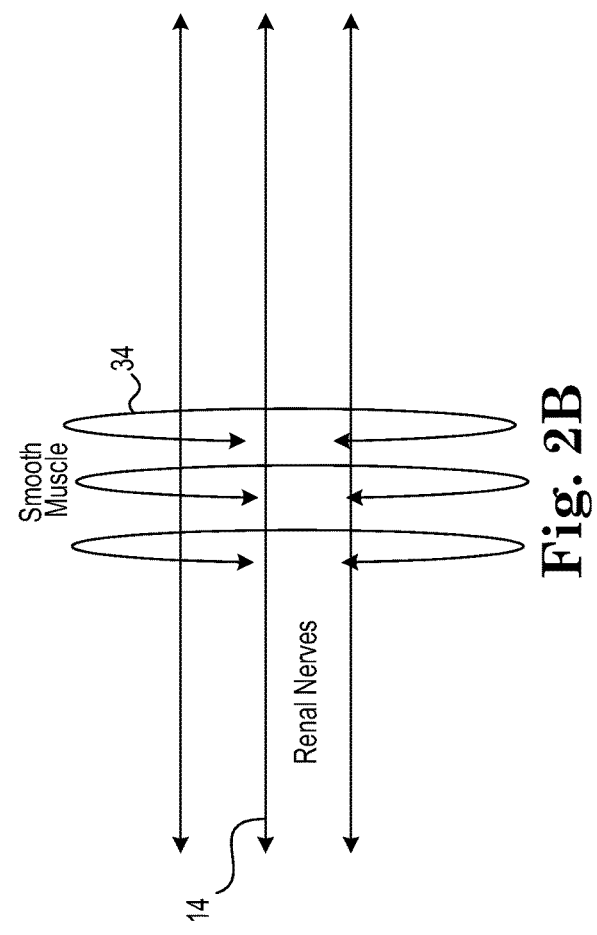
Fig. 2A
Fig. 2B

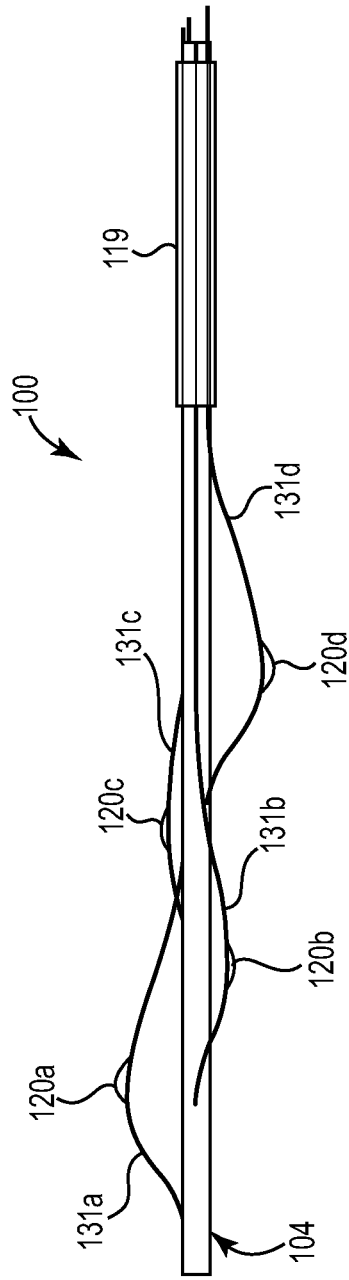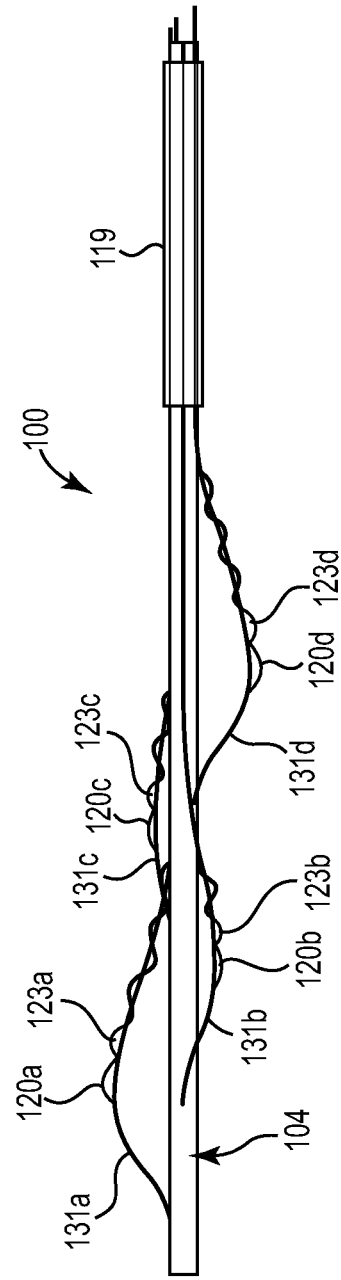

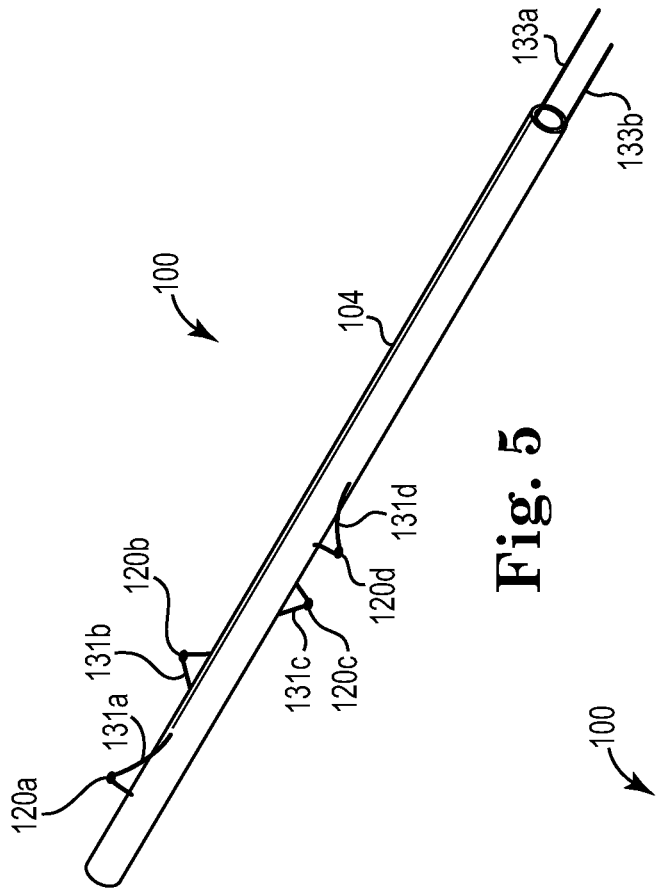
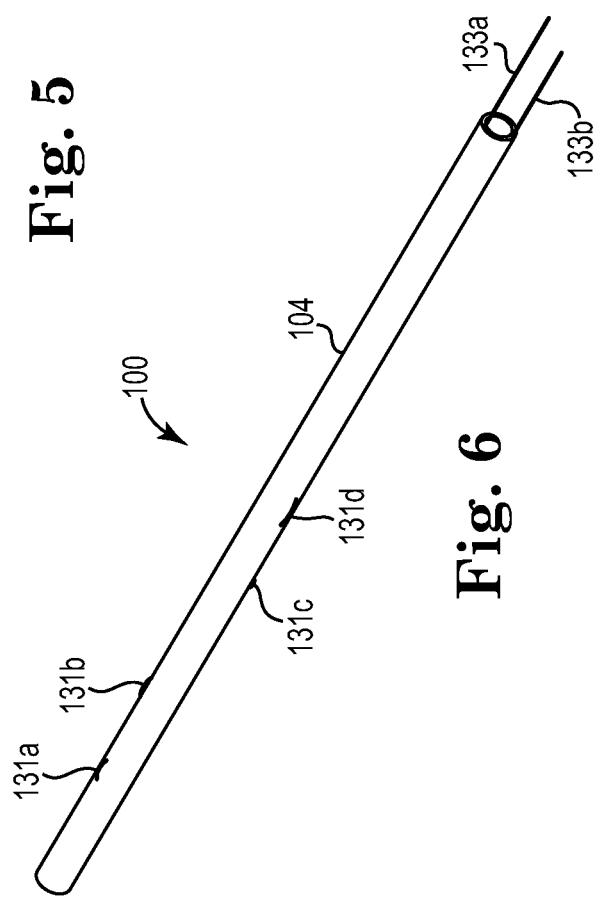

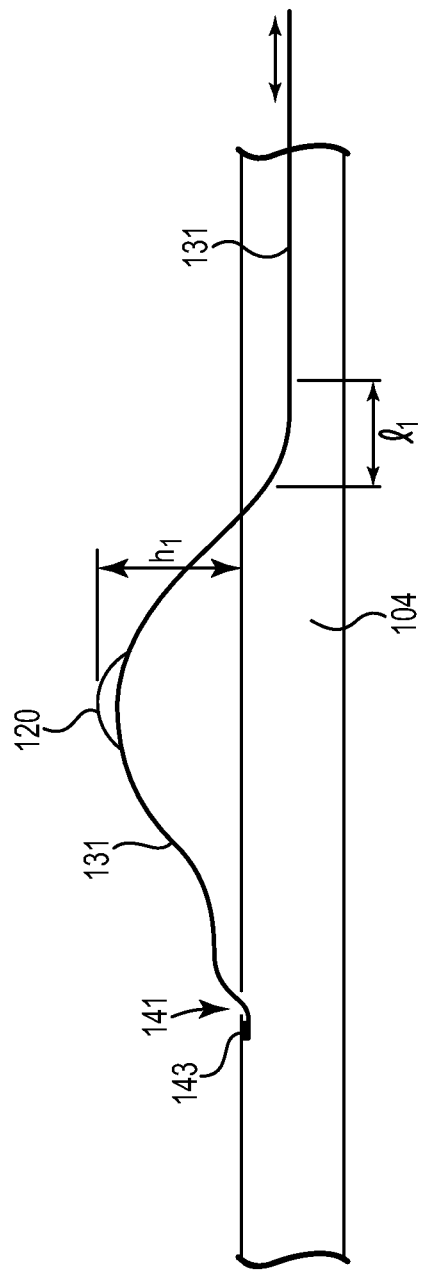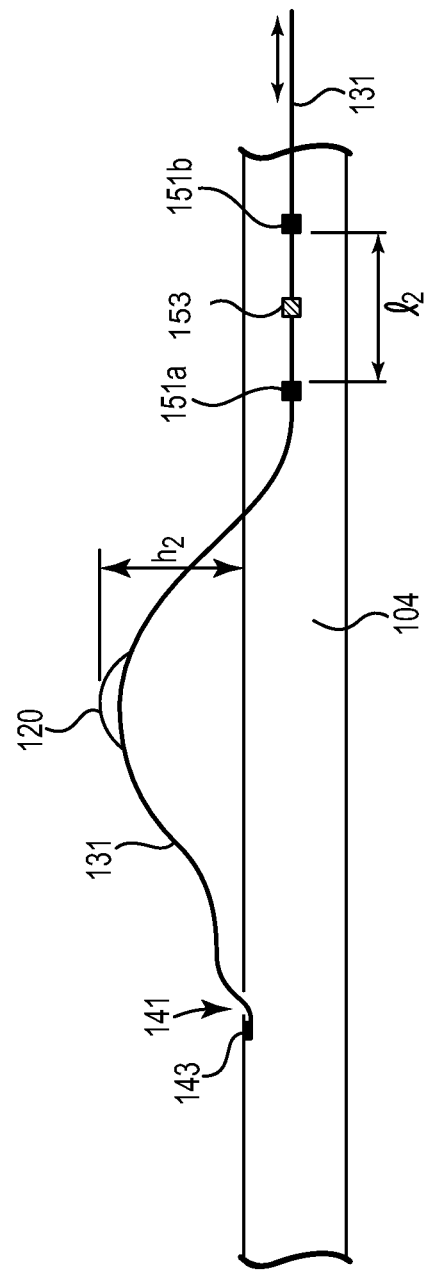

RF ELECTRODES ON MULTIPLE FLEXIBLE WIRES FOR RENAL NERVE ABLATION

CROSS-REFERENCE TO RELATED APPLICATIONS

This application is a continuation of patent application Ser. No. 13/184,677, filed on Jul. 18, 2011, now U.S. Pat. No. 9,408,661; which claims the benefit of Provisional Patent Application Ser. No. 61/369,458, filed Jul. 30, 2010, and 61/418,667 filed Dec. 1, 2010, to which priority is claimed pursuant to 35 U.S.C. § 119(e) and which are hereby incorporated by reference in their entirety.

SUMMARY

Embodiments of the disclosure are generally directed to apparatuses and methods for ablating target tissue of the body from within a vessel. Embodiments are directed to high frequency AC (e.g., radiofrequency (RF)) ablation catheters, systems, and methods that employ electrodes on multiple flexible wires for enhanced apposition of electrodes within a target vessel, particularly for irregularities along the inner wall of the vessel. Various embodiments of the disclosure are directed to apparatuses and methods for ablating perivascular renal nerves, such as for treatment of hypertension.

According to various embodiments, an apparatus for delivering ablation therapy includes a sheath having a lumen and a length of the shaft sufficient to access a target vessel within a patient relative to a percutaneous access location. A catheter comprises a flexible shaft having a proximal end, a distal end, and a length, the length of the shaft sufficient to access the target vessel relative to the percutaneous access location. The shaft is dimensioned for displacement within the lumen of the sheath and extendible beyond a distal tip of the sheath.

The apparatus includes a plurality of elongated resilient members each mounted along a longitudinal length of the distal end of the shaft. The resilient members engage the shaft at a number of longitudinally spaced-apart locations and are extensible radially from the shaft at regions defined between the longitudinally spaced-apart engagement locations. One or more electrodes are mounted on each of the resilient members at the radially extensible regions. A number of conductors are electrically coupled to the electrodes and extend along the shaft of the catheter. The elongated resilient members are collapsible when encompassed within the lumen of the sheath and extensible radially outward from the shaft at the regions defined between the longitudinally spaced-apart engagement locations when the catheter and the resilient members are axially extended beyond the distal tip of the sheath.

In accordance with some embodiments, an apparatus includes a sheath having a lumen and a length sufficient to access a patient's renal artery relative to a percutaneous access location. A catheter comprises a flexible shaft having a proximal end, a distal end, and a length, the length of the shaft sufficient to access a patient's renal artery relative to the percutaneous access location, The shaft is dimensioned for displacement within the lumen of the sheath and is extendible beyond a distal tip of the sheath.

The apparatus includes a number of elongated resilient members each mounted along a longitudinal length of the distal end of the shaft. The resilient members engage the shaft at a number of longitudinally spaced-apart locations and are extensible radially from the shaft at regions defined between the longitudinally spaced-apart engagement locations. One or more electrodes are mounted on each of the resilient members at the radially extensible regions. A number of conductors are electrically coupled to the electrodes and extend along the shaft of the catheter. The elongated resilient members are collapsible when encompassed within the lumen of the sheath and extensible radially outward from the shaft at the regions defined between the longitudinally spaced-apart engagement locations when the catheter and the resilient members are axially extended beyond the distal tip of the sheath.

These and other features can be understood in view of the following detailed discussion and the accompanying drawings.

BRIEF DESCRIPTION OF THE DRAWINGS

FIGS. 2A and 2B illustrate sympathetic innervation of the renal artery;

FIG. 4A illustrates an apparatus for ablating target tissue of a vessel of the body in accordance with various embodiments;

FIG. 4B illustrates an apparatus for ablating target tissue of a vessel of the body in accordance with various embodiments;

FIGS. 5 and 6 illustrate the distal end of a catheter shaft which supports a wire segment arrangement and a retraction mechanism in accordance with low-profile embodiments of the disclosure;

FIGS. 9 and 10 illustrate arrangements that facilitate controllable expansion and retraction of a wire segment arrangement in accordance with various embodiments;

DISCLOSURE

Figure 1:
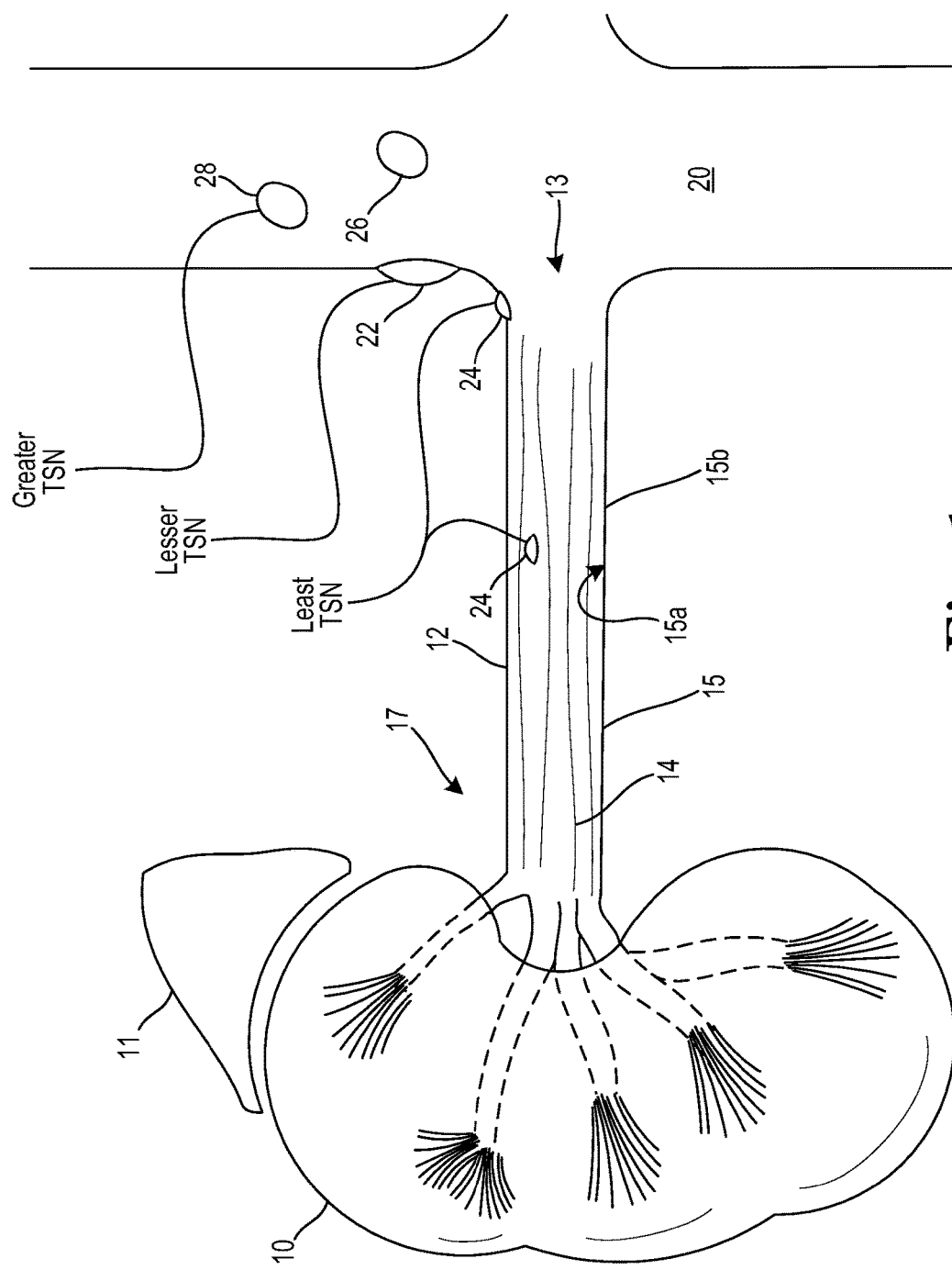
FIG. 1 is an illustration of a right kidney and renal vasculature including a renal artery branching laterally from the abdominal aorta.

Embodiments of the disclosure are directed to apparatuses and methods for ablating target tissue from within a vessel. Embodiments of the disclosure are directed to apparatuses and methods for ablating of perivascular renal nerves from within the renal artery for the treatment of hypertension. Embodiments of the disclosure include wire segment structures that support a multiplicity of electrodes for delivering renal nerve ablation.

Obtaining good contact with the artery wall during ablation of perivascular renal nerves has been difficult. If contact is variable, the tissue temperatures are not well controlled, and an ablative temperature may not be achieved in the target tissue, while temperature in other areas, such as portions of the artery wall, may deviate enough to cause unwanted arterial tissue injury. For ideal anatomy, good vessel apposition can be achieved more easily, but especially with tortuous or diseased renal arteries, there can be very poor contact to effectively and predictably transfer electrical current from an ablation device to the tissue. Controlled ablation at multiple discrete regions may be desired to reduce arterial injury, without requiring multiple repositioning and ablation cycles. There is continued need for improved vessel wall contact and multi-site ablation for nerve ablation and other therapies.

Embodiments of the disclosure are directed to apparatuses and methods for multi-site RF ablation of perivascular renal nerves for hypertension treatment. According to various embodiments, an intravascular catheter device has multiple wire segments near the distal end which move between low-profile introduction configuration and larger-diameter deployed configuration. One or more RF electrodes are mounted on separate wire segments. The wire segments can comprise expandable curves, loops, mesh, basket, or other structures to place the RF electrodes in separate locations.

When the wire segment structures are deployed, they flex to accommodate varying vessel anatomy. Wire segment deployment can be coupled as in a fixed basket configuration, or independent so that each wire segment expands as much as the anatomy requires. Deployment of the wire segments places the RF electrodes in good contact with the vessel wall.

The catheter device can be advanced and deployed in a renal artery to ablate the renal nerves. Activating certain RF electrodes or combinations by energizing from an external energy source through insulated conductors along the catheter, provides multiple discrete RF ablation regions. Deployment can utilize self-expanding elastic forces, push/pull control structures, external retaining and recapture sheath, and other linkages and structures. An external sheath can be used to protect and constrain the wire segments at the distal end of the catheter during placement and withdrawal.

According to various embodiments, an intravascular catheter device has multiple wire segments near the distal end which move between low-profile introduction configuration and larger-diameter deployed configuration. One or more RF electrodes are mounted on separate wire segments. The wire segments can comprise expandable curves, loops, mesh, basket, or other structures to place the RF electrodes in separate locations. When the wire segment structures are deployed, they flex to accommodate varying vessel anatomy.

In one configuration, the wire segments are independent of other wires, so that each wire segment expands as much as the anatomy requires. The wire segments can be insulated and serve as electrical conductors between an external RF control unit and the electrodes. Activating certain RF electrodes or combinations by energizing from an external energy source through insulated conductors along the catheter, provides multiple discrete RF ablation regions. Deployment can utilize self-expanding elastic forces, push/pull control structures, external retaining and recapture sheath, and other linkages and structures.

Deployment of the wire segments places the RF electrodes in good contact with the vessel wall. An external sheath can be used to protect and constrain the wire segments at the distal end of the catheter during placement and withdrawal. The catheter device can be advanced and deployed in a renal artery to ablate the renal nerves. After positioning the catheter's distal end within the renal artery, the sheath can be retracted to allow the wire segments to deploy and expand.

In other embodiments, the wire segments can be coupled as in a fixed basket configuration, much like a mapping catheter. Some or all electrodes can be energized simultaneously, or individual electrodes or subsets of the electrodes can be energized to ablate one or more regions of the perivascular nerves. Variations include number, circumferential location, and axial location of wire segments and electrodes. Wire segments can have spiral or other curvature. Wire segments can be configured as loops.

The proximal ends of the wires can be pushed or pulled to aid in deployment. The distal ends of the wire segments can be affixed to the catheter. Lumen segments, or sliding attachment points, can be provided to control the wires but allow deployment movements.

Multiple wire segments with electrodes can be incorporated into a catheter, with push-pull deployment of the wire segments. Electrodes can be shaped to displace tissue of the inner artery wall toward the outer artery wall so as to effectively shorten the distance separating the electrode and the innervated target tissue adjacent the outer artery wall. The electrodes, according to various embodiments, include a tissue displacing tip having a radius that forcibly pushes the inner artery wall into the outer artery wall (thereby compressing intervening artery wall tissue) without penetrating the inner or outer artery walls. In some embodiments, it may be desirable the permit the electrode tip to penetrate through the inner artery wall, but preferably not the outer artery wall. An external sheath can be used to cover the wires and electrodes during advancement and retraction.

One or more temperature sensors, such as thermocouples, can be provided at the site of the electrodes to measure the temperature of the electrodes. In some embodiments, a temperature sensor is positioned near or at the site of each electrode, allowing for precision temperature measurements at individual electrode locations of the ablation electrode arrangement.

Various embodiments of the disclosure are directed to apparatuses and methods for renal denervation for treating hypertension. Hypertension is a chronic medical condition in which the blood pressure is elevated. Persistent hypertension is a significant risk factor associated with a variety of adverse medical conditions, including heart attacks, heart failure, arterial aneurysms, and strokes. Persistent hypertension is a leading cause of chronic renal failure. Hyperactivity of the sympathetic nervous system serving the kidneys is associated with hypertension and its progression. Deactivation of nerves in the kidneys via renal denervation can reduce blood pressure, and may be a viable treatment option for many patients with hypertension who do not respond to conventional drugs.

The kidneys are instrumental in a number of body processes, including blood filtration, regulation of fluid balance, blood pressure control, electrolyte balance, and hormone production. One primary function of the kidneys is to remove toxins, mineral salts, and water from the blood to form urine. The kidneys receive about 20-25% of cardiac output through the renal arteries that branch left and right from the abdominal aorta, entering each kidney at the concave surface of the kidneys, the renal hilum.

Blood flows into the kidneys through the renal artery and the afferent arteriole, entering the filtration portion of the kidney, the renal corpuscle. The renal corpuscle is composed of the glomerulus, a thicket of capillaries, surrounded by a fluid-filled, cup-like sac called Bowman's capsule. Solutes in the blood are filtered through the very thin capillary walls of the glomerulus due to the pressure gradient that exists between the blood in the capillaries and the fluid in the Bowman's capsule. The pressure gradient is controlled by the contraction or dilation of the arterioles. After filtration occurs, the filtered blood moves through the efferent arteriole and the peritubular capillaries, converging in the interlobular veins, and finally exiting the kidney through the renal vein.

Particles and fluid filtered from the blood move from the Bowman's capsule through a number of tubules to a collecting duct. Urine is formed in the collecting duct and then exits through the ureter and bladder. The tubules are surrounded by the peritubular capillaries (containing the filtered blood). As the filtrate moves through the tubules and toward the collecting duct, nutrients, water, and electrolytes, such as sodium and chloride, are reabsorbed into the blood.

The kidneys are innervated by the renal plexus which emanates primarily from the aorticorenal ganglion. Renal ganglia are formed by the nerves of the renal plexus as the nerves follow along the course of the renal artery and into the kidney. The renal nerves are part of the autonomic nervous system which includes sympathetic and parasympathetic components. The sympathetic nervous system is known to be the system that provides the bodies "fight or flight" response, whereas the parasympathetic nervous system provides the "rest and digest" response. Stimulation of sympathetic nerve activity triggers the sympathetic response which causes the kidneys to increase production of hormones that increase vasoconstriction and fluid retention. This process is referred to as the renin-angiotensin-aldosterone-system (RAAS) response to increased renal sympathetic nerve activity.

In response to a reduction in blood volume, the kidneys secrete renin, which stimulates the production of angiotensin. Angiotensin causes blood vessels to constrict, resulting in increased blood pressure, and also stimulates the secretion of the hormone aldosterone from the adrenal cortex. Aldosterone causes the tubules of the kidneys to increase the reabsorption of sodium and water, which increases the volume of fluid in the body and blood pressure.

Congestive heart failure (CHF) is a condition that has been linked to kidney function. CHF occurs when the heart is unable to pump blood effectively throughout the body. When blood flow drops, renal function degrades because of insufficient perfusion of the blood within the renal corpuscles. The decreased blood flow to the kidneys triggers an increase in sympathetic nervous system activity (i.e., the RAAS becomes too active) that causes the kidneys to secrete hormones that increase fluid retention and vasorestriction. Fluid retention and vasorestriction in turn increases the peripheral resistance of the circulatory system, placing an even greater load on the heart, which diminishes blood flow further. If the deterioration in cardiac and renal functioning continues, eventually the body becomes overwhelmed, and an episode of heart failure decompensation occurs, often leading to hospitalization of the patient.

FIG. 1 is an illustration of a right kidney 10 and renal vasculature including a renal artery 12 branching laterally from the abdominal aorta 20. In FIG. 1, only the right kidney 10 is shown for purposes of simplicity of explanation, but reference will be made herein to both right and left kidneys and associated renal vasculature and nervous system structures, all of which are contemplated within the context of embodiments of the disclosure. The renal artery 12 is purposefully shown to be disproportionately larger than the right kidney 10 and abdominal aorta 20 in order to facilitate discussion of various features and embodiments of the present disclosure.

The right and left kidneys are supplied with blood from the right and left renal arteries that branch from respective right and left lateral surfaces of the abdominal aorta 20. Each of the right and left renal arteries is directed across the crus of the diaphragm, so as to form nearly a right angle with the abdominal aorta 20. The right and left renal arteries extend generally from the abdominal aorta 20 to respective renal sinuses proximate the hilum 17 of the kidneys, and branch into segmental arteries and then interlobular arteries within the kidney 10. The interlobular arteries radiate outward, penetrating the renal capsule and extending through the renal columns between the renal pyramids. Typically, the kidneys receive about 20% of total cardiac output which, for normal persons, represents about 1200 mL of blood flow through the kidneys per minute.

The primary function of the kidneys is to maintain water and electrolyte balance for the body by controlling the production and concentration of urine. In producing urine, the kidneys excrete wastes such as urea and ammonium. The kidneys also control reabsorption of glucose and amino acids, and are important in the production of hormones including vitamin D, renin and erythropoietin.

An important secondary function of the kidneys is to control metabolic homeostasis of the body. Controlling hemostatic functions include regulating electrolytes, acid-base balance, and blood pressure. For example, the kidneys are responsible for regulating blood volume and pressure by adjusting volume of water lost in the urine and releasing erythropoietin and renin, for example. The kidneys also regulate plasma ion concentrations (e.g., sodium, potassium, chloride ions, and calcium ion levels) by controlling the quantities lost in the urine and the synthesis of calcitrol. Other hemostatic functions controlled by the kidneys include stabilizing blood pH by controlling loss of hydrogen and bicarbonate ions in the urine, conserving valuable nutrients by preventing their excretion, and assisting the liver with detoxification.

Also shown in FIG. 1 is the right suprarenal gland 11, commonly referred to as the right adrenal gland. The suprarenal gland 11 is a star-shaped endocrine gland that rests on top of the kidney 10. The primary function of the suprarenal glands (left and right) is to regulate the stress response of the body through the synthesis of corticosteroids and catecholamines, including cortisol and adrenaline (epinephrine), respectively. Encompassing the kidneys 10, suprarenal glands 11, renal vessels 12, and adjacent perirenal fat is the renal fascia, e.g., Gerota's fascia, (not shown), which is a fascial pouch derived from extraperitoneal connective tissue.

The autonomic nervous system of the body controls involuntary actions of the smooth muscles in blood vessels, the digestive system, heart, and glands. The autonomic nervous system is divided into the sympathetic nervous system and the parasympathetic nervous system. In general terms, the parasympathetic nervous system prepares the body for rest by lowering heart rate, lowering blood pressure, and stimulating digestion. The sympathetic nervous system effectuates the body's fight-or-flight response by increasing heart rate, increasing blood pressure, and increasing metabolism.

In the autonomic nervous system, fibers originating from the central nervous system and extending to the various ganglia are referred to as preganglionic fibers, while those extending from the ganglia to the effector organ are referred to as postganglionic fibers. Activation of the sympathetic nervous system is effected through the release of adrenaline (epinephrine) and to a lesser extent norepinephrine from the suprarenal glands 11. This release of adrenaline is triggered by the neurotransmitter acetylcholine released from preganglionic sympathetic nerves.

The kidneys and ureters (not shown) are innervated by the renal nerves 14. FIGS. 1 and 2A-2B illustrate sympathetic innervation of the renal vasculature, primarily innervation of the renal artery 12. The primary functions of sympathetic innervation of the renal vasculature include regulation of renal blood flow and pressure, stimulation of renin release, and direct stimulation of water and sodium ion reabsorption.

Most of the nerves innervating the renal vasculature are sympathetic postganglionic fibers arising from the superior mesenteric ganglion 26. The renal nerves 14 extend generally axially along the renal arteries 12, enter the kidneys 10 at the hilum 17, follow the branches of the renal arteries 12 within the kidney 10, and extend to individual nephrons. Other renal ganglia, such as the renal ganglia 24, superior mesenteric ganglion 26, the left and right aorticorenal ganglia 22, and celiac ganglia 28 also innervate the renal vasculature. The celiac ganglion 28 is joined by the greater thoracic splanchnic nerve (greater TSN). The aorticorenal ganglia 26 is joined by the lesser thoracic splanchnic nerve (lesser TSN) and innervates the greater part of the renal plexus.

Sympathetic signals to the kidney 10 are communicated via innervated renal vasculature that originates primarily at spinal segments T10-T12 and L1. Parasympathetic signals originate primarily at spinal segments S2-S4 and from the medulla oblongata of the lower brain. Sympathetic nerve traffic travels through the sympathetic trunk ganglia, where some may synapse, while others synapse at the aorticorenal ganglion 22 (via the lesser thoracic splanchnic nerve, i.e., lesser TSN) and the renal ganglion 24 (via the least thoracic splanchnic nerve, i.e., least TSN). The postsynaptic sympathetic signals then travel along nerves 14 of the renal artery 12 to the kidney 10. Presynaptic parasympathetic signals travel to sites near the kidney 10 before they synapse on or near the kidney 10.

With particular reference to FIG. 2A, the renal artery 12, as with most arteries and arterioles, is lined with smooth muscle 34 that controls the diameter of the renal artery lumen 13. Smooth muscle, in general, is an involuntary non-striated muscle found within the media layer of large and small arteries and veins, as well as various organs. The glomeruli of the kidneys, for example, contain a smooth muscle-like cell called the mesangial cell. Smooth muscle is fundamentally different from skeletal muscle and cardiac muscle in terms of structure, function, excitation-contraction coupling, and mechanism of contraction.

Smooth muscle cells can be stimulated to contract or relax by the autonomic nervous system, but can also react on stimuli from neighboring cells and in response to hormones and blood borne electrolytes and agents (e.g., vasodilators or vasoconstrictors). Specialized smooth muscle cells within the afferent arteriole of the juxtaglomerular apparatus of kidney 10, for example, produces renin which activates the angiotension II system.

The renal nerves 14 innervate the smooth muscle 34 of the renal artery wall 15 and extend lengthwise in a generally axial or longitudinal manner along the renal artery wall 15. The smooth muscle 34 surrounds the renal artery circumferentially, and extends lengthwise in a direction generally transverse to the longitudinal orientation of the renal nerves 14, as is depicted in FIG. 2B.

The smooth muscle 34 of the renal artery 12 is under involuntary control of the autonomic nervous system. An increase in sympathetic activity, for example, tends to contract the smooth muscle 34, which reduces the diameter of the renal artery lumen 13 and decreases blood perfusion. A decrease in sympathetic activity tends to cause the smooth muscle 34 to relax, resulting in vessel dilation and an increase in the renal artery lumen diameter and blood perfusion. Conversely, increased parasympathetic activity tends to relax the smooth muscle 34, while decreased parasympathetic activity tends to cause smooth muscle contraction.

Figure 3A:
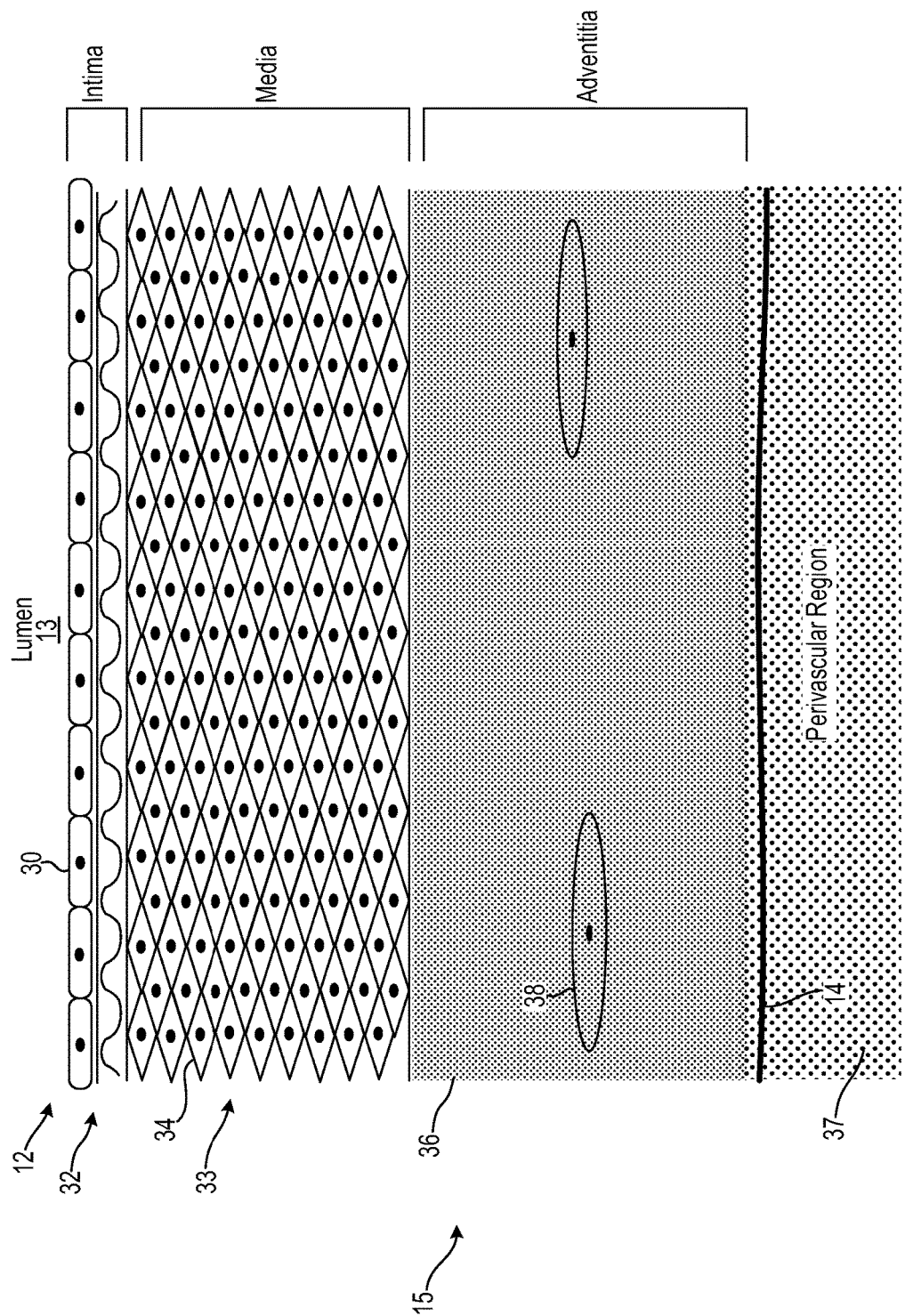
FIG. 3A illustrates various tissue layers of the wall of the renal artery.

FIG. 3A shows a segment of a longitudinal cross-section through a renal artery, and illustrates various tissue layers of the wall 15 of the renal artery 12. The innermost layer of the renal artery 12 is the endothelium 30, which is the innermost layer of the intima 32 and is supported by an internal elastic membrane. The endothelium 30 is a single layer of cells that contacts the blood flowing though the vessel lumen 13. Endothelium cells are typically polygonal, oval, or fusiform, and have very distinct round or oval nuclei. Cells of the endothelium 30 are involved in several vascular functions, including control of blood pressure by way of vasoconstriction and vasodilation, blood clotting, and acting as a barrier layer between contents within the lumen 13 and surrounding tissue, such as the membrane of the intima 32 separating the intima 32 from the media 34, and the adventitia 36. The membrane or maceration of the intima 32 is a fine, transparent, colorless structure which is highly elastic, and commonly has a longitudinal corrugated pattern.

Adjacent the intima 32 is the media 33, which is the middle layer of the renal artery 12. The media is made up of smooth muscle 34 and elastic tissue. The media 33 can be readily identified by its color and by the transverse arrangement of its fibers. More particularly, the media 33 consists principally of bundles of smooth muscle fibers 34 arranged in a thin plate-like manner or lamellae and disposed circularly around the arterial wall 15. The outermost layer of the renal artery wall 15 is the adventitia 36, which is made up of connective tissue. The adventitia 36 includes fibroblast cells 38 that play an important role in wound healing.

A perivascular region 37 is shown adjacent and peripheral to the adventitia 36 of the renal artery wall 15. A renal nerve 14 is shown proximate the adventitia 36 and passing through a portion of the perivascular region 37. The renal nerve 14 is shown extending substantially longitudinally along the outer wall 15 of the renal artery 12. The main trunk of the renal nerves 14 generally lies in or on the adventitia 36 of the renal artery 12, often passing through the perivascular region 37, with certain branches coursing into the media 33 to enervate the renal artery smooth muscle 34.

Embodiments of the disclosure may be implemented to provide varying degrees of denervation therapy to innervated renal vasculature. For example, embodiments of the disclosure may provide for control of the extent and relative permanency of renal nerve impulse transmission interruption achieved by denervation therapy delivered using a treatment apparatus of the disclosure. The extent and relative permanency of renal nerve injury may be tailored to achieve a desired reduction in sympathetic nerve activity (including a partial or complete block) and to achieve a desired degree of permanency (including temporary or irreversible injury).

Figure 3B:
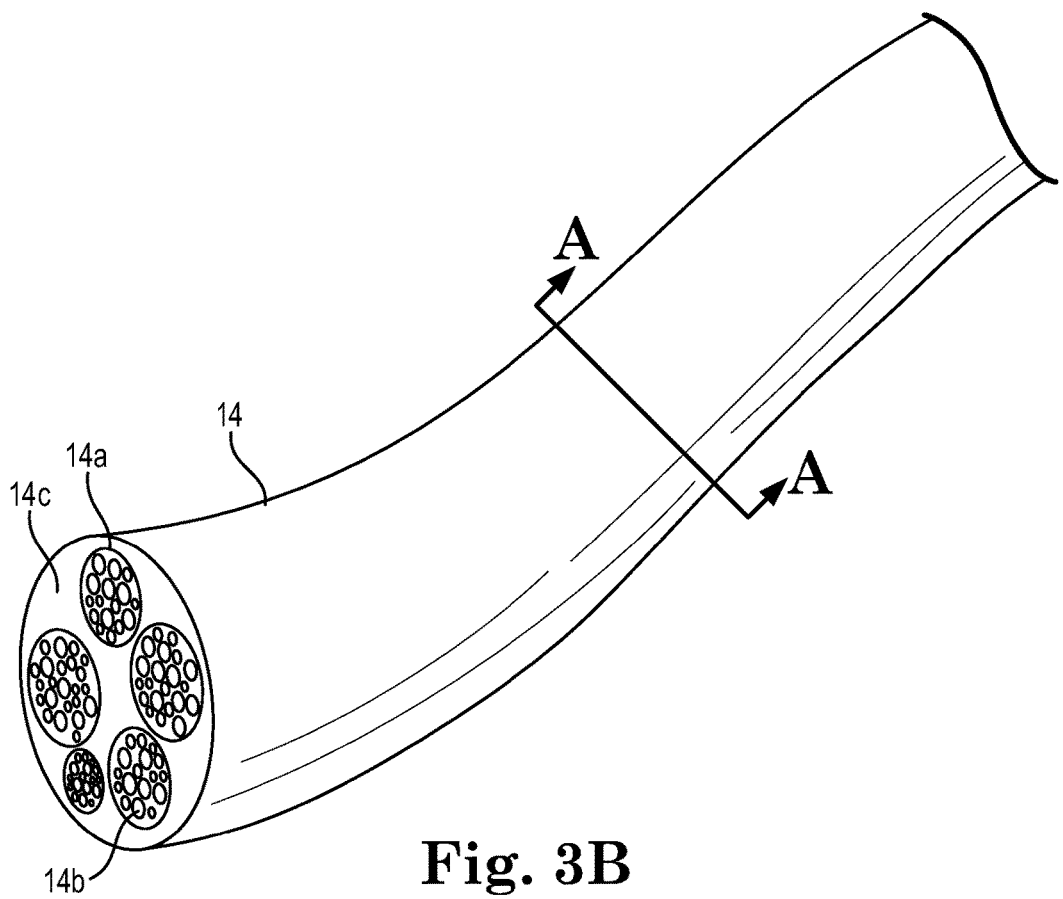
FIGS. 3B and 3C illustrate a portion of a renal nerve.
Figure 3C:
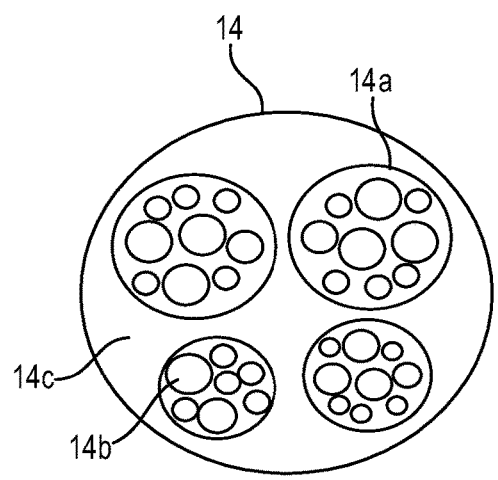

Returning to FIGS. 3B and 3C, the portion of the renal nerve 14 shown in FIGS. 3B and 3C includes bundles 14a of nerve fibers 14b each comprising axons or dendrites that originate or terminate on cell bodies or neurons located in ganglia or on the spinal cord, or in the brain. Supporting tissue structures 14c of the nerve 14 include the endoneurium (surrounding nerve axon fibers), perineurium (surrounds fiber groups to form a fascicle), and epineurium (binds fascicles into nerves), which serve to separate and support nerve fibers 14b and bundles 14a. In particular, the endoneurium, also referred to as the endoneurium tube or tubule, is a layer of delicate connective tissue that encloses the myelin sheath of a nerve fiber 14b within a fasciculus.

Major components of a neuron include the soma, which is the central part of the neuron that includes the nucleus, cellular extensions called dendrites, and axons, which are cable-like projections that carry nerve signals. The axon terminal contains synapses, which are specialized structures where neurotransmitter chemicals are released in order to communicate with target tissues. The axons of many neurons of the peripheral nervous system are sheathed in myelin, which is formed by a type of glial cell known as Schwann cells. The myelinating Schwann cells are wrapped around the axon, leaving the axolemma relatively uncovered at regularly spaced nodes, called nodes of Ranvier. Myelination of axons enables an especially rapid mode of electrical impulse propagation called saltation.

In some embodiments, a treatment apparatus of the disclosure may be implemented to deliver denervation therapy that causes transient and reversible injury to renal nerve fibers 14b. In other embodiments, a treatment apparatus of the disclosure may be implemented to deliver denervation therapy that causes more severe injury to renal nerve fibers 14b, which may be reversible if the therapy is terminated in a timely manner. In preferred embodiments, a treatment apparatus of the disclosure may be implemented to deliver denervation therapy that causes severe and irreversible injury to renal nerve fibers 14b, resulting in permanent cessation of renal sympathetic nerve activity. For example, a treatment apparatus may be implemented to deliver a denervation therapy that disrupts nerve fiber morphology to a degree sufficient to physically separate the endoneurium tube of the nerve fiber 14b, which can prevent regeneration and re-innervation processes.

By way of example, and in accordance with Seddon's classification as is known in the art, a treatment apparatus of the disclosure may be implemented to deliver a denervation therapy that interrupts conduction of nerve impulses along the renal nerve fibers 14b by imparting damage to the renal nerve fibers 14b consistent with neurapraxia. Neurapraxia describes nerve damage in which there is no disruption of the nerve fiber 14b or its sheath. In this case, there is an interruption in conduction of the nerve impulse down the nerve fiber, with recovery taking place within hours to months without true regeneration, as Wallerian degeneration does not occur. Wallerian degeneration refers to a process in which the part of the axon separated from the neuron's cell nucleus degenerates. This process is also known as anterograde degeneration. Neurapraxia is the mildest form of nerve injury that may be imparted to renal nerve fibers 14b by use of a treatment apparatus according to embodiments of the disclosure.

A treatment apparatus may be implemented to interrupt conduction of nerve impulses along the renal nerve fibers 14b by imparting damage to the renal nerve fibers consistent with axonotmesis. Axonotmesis involves loss of the relative continuity of the axon of a nerve fiber and its covering of myelin, but preservation of the connective tissue framework of the nerve fiber. In this case, the encapsulating support tissue 14c of the nerve fiber 14b are preserved. Because axonal continuity is lost, Wallerian degeneration occurs. Recovery from axonotmesis occurs only through regeneration of the axons, a process requiring time on the order of several weeks or months. Electrically, the nerve fiber 14b shows rapid and complete degeneration. Regeneration and re-innervation may occur as long as the endoneural tubes are intact.

A treatment apparatus may be implemented to interrupt conduction of nerve impulses along the renal nerve fibers 14b by imparting damage to the renal nerve fibers 14b consistent with neurotmesis. Neurotmesis, according to Seddon's classification, is the most serious nerve injury in the scheme. In this type of injury, both the nerve fiber 14b and the nerve sheath are disrupted. While partial recovery may occur, complete recovery is not possible. Neurotmesis involves loss of continuity of the axon and the encapsulating connective tissue 14c, resulting in a complete loss of autonomic function, in the case of renal nerve fibers 14b. If the nerve fiber 14b has been completely divided, axonal regeneration causes a neuroma to form in the proximal stump.

A more stratified classification of neurotmesis nerve damage may be found by reference to the Sunderland System as is known in the art. The Sunderland System defines five degrees of nerve damage, the first two of which correspond closely with neurapraxia and axonotmesis of Seddon's classification. The latter three Sunderland System classifications describe different levels of neurotmesis nerve damage.

The first and second degrees of nerve injury in the Sunderland system are analogous to Seddon's neurapraxia and axonotmesis, respectively. Third degree nerve injury, according to the Sunderland System, involves disruption of the endoneurium, with the epineurium and perineurium remaining intact. Recovery may range from poor to complete depending on the degree of intrafascicular fibrosis. A fourth degree nerve injury involves interruption of all neural and supporting elements, with the epineurium remaining intact. The nerve is usually enlarged. Fifth degree nerve injury involves complete transection of the nerve fiber 14b with loss of continuity.

Turning now to FIG. 4A, there is illustrated an apparatus for ablating target tissue of a vessel of the body in accordance with various embodiments. According to some embodiments, and as shown in FIG. 4A, the apparatus includes a sheath 119 having a lumen and a length sufficient to access a target vessel of a patient, such as the patient's renal artery, relative to a percutaneous access location. The apparatus further includes a catheter 100 which includes a flexible shaft 104 having a proximal end, a distal end, and a length. The length of the shaft 104 is sufficient to access the target vessel, such as a patient's renal artery 12, relative to a percutaneous access location. The shaft 104 of the catheter 100 is dimensioned for displacement within the lumen of the sheath 119, and is extendible beyond a distal tip of the sheath 119.

A multiplicity of elongated resilient members 131 are provided at the distal end of the catheter's shaft 104. In the representative embodiment shown in FIG. 4A, four elongated resilient members 131a-131d are provided at the distal end of the catheter's shaft 104. Each of the elongated resilient members 131a-131d is mounted along a longitudinal length of the distal end of the shaft 104, and engages the shaft 104 at two or more longitudinally spaced-apart locations. The elongated resilient members 131a-131d are mounted on the shaft 104 so that each is extensible radially from the shaft 104 at regions defined between the longitudinally spaced-apart engagement locations. The elongated resilient members 131a-131d are formed of a material that produces elastic forces in the resilient members 131a-131d sufficient to cause self-expansion of the resilient members 131a-131d when the catheter 100 and the resilient members 131a-131d are axially extended beyond the distal tip of the shaft 104. For example, the resilient members 131a-131d can be formed from a flexible electrically conductive material that facilitates flexing of the resilient members 131a-131d to accommodate variations in renal artery anatomy.

One or more electrodes 120 are mounted on each of the resilient members 131a-131d at the radially extensible regions. In the representative embodiment shown in FIG. 4A, one electrode 120a-120d is shown mounted on each of the four resilient members 131a-131d at an apex location between longitudinally spaced-apart engagement locations of the shaft 104. A conductor arrangement electrically couples to the one or more electrodes 120 mounted on each of the resilient members 131a-131d and extends along the shaft 104 to a proximal end of the catheter 100.

In some embodiments, each of the resilient members 131a-131d defines a conductor that extends along the shaft 104 and provides for electrical connectivity with the electrodes 120a-120d at a proximal end of the catheter 100. The resilient members 131a-131 can be covered with an insulating sleeve or coating over the region that extends along the length of the shaft 104. In other embodiments, separate lumens of the shaft 104 may be dimensioned to receive one of the resilient members 131a-131d, which may include an inner wall of insulating material in resilient member configurations that do not include an insulating sleeve or coating. In further embodiments, each of the resilient members 131a-131d can be coupled to a respective electrical conductor near the distal end of the catheter 100, and the electrical conductors can extend along the shaft and be accessible at the proximal end of the catheter 100.

Figure 4C:
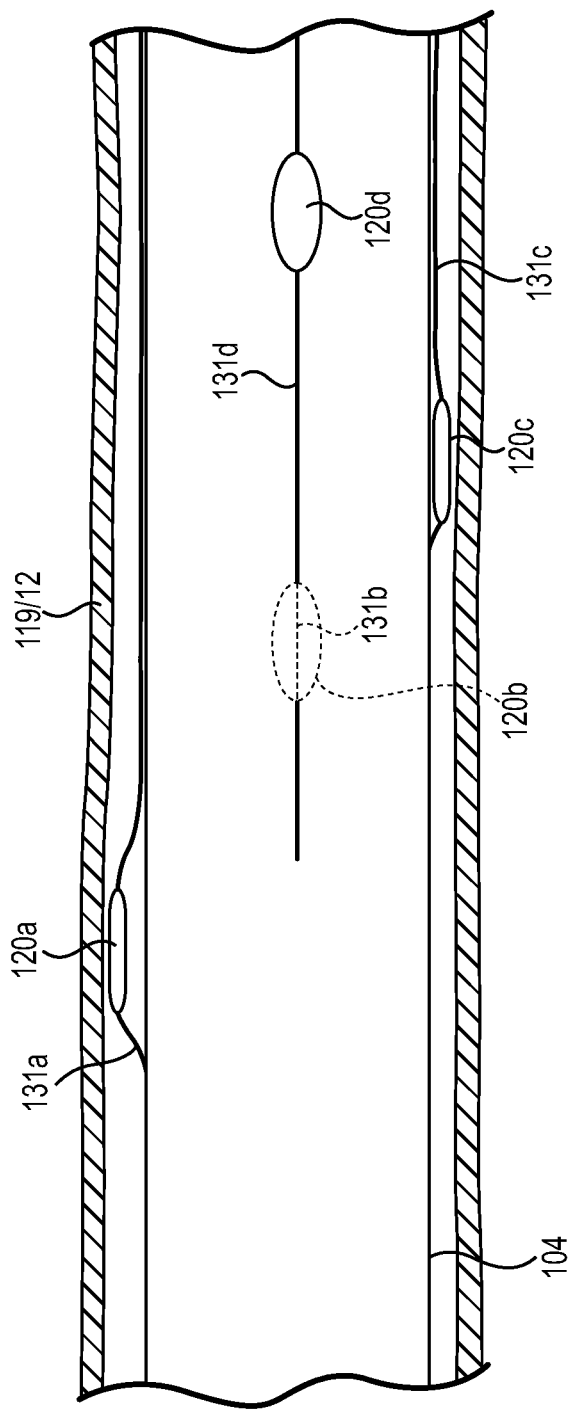
FIG. 4C shows the elongated resilient members of a ablation treatment element in a collapsed configuration when encompassed within the lumen of a sheath or a target vessel.

The elongated resilient members 131a-131d are preferably constructed from a resilient conductive alloy that has a shape memory. As is best seen in FIG. 4C, the elongated resilient members 131a-131d are collapsible when encompassed within the lumen of the sheath 119 or within the lumen of a target vessel, such as a patient's renal artery 12. When axially extended beyond the distal tip of the sheath 119, the resilient members 131a-131d expand radially outwardly from the shaft 104 at the regions defined between the longitudinally spaced-apart engagement locations. The electrodes 120a-120d mounted at or near apical locations of the resilient members 131a-131d are moved outwardly and into forced engagement with the inner wall of the target vessel by the outwardly expanding resilient member 131a-131d. In the deployed configuration, the multiple resilient members 131a-131d provide for enhanced apposition of the electrodes 120a-120d within the target vessel, particularly for irregularities along the inner wall of the vessel.

According to various embodiments, the resilient members 131a-131d are arranged about a perimeter of the catheter's shaft 104 so that the electrodes 120a-120d are positioned at disparate locations of a wall of the target vessel, such as the renal artery. For example, the resilient members 131a-131d are arranged about the perimeter of the catheter's shaft 104 so that the electrodes 120a-120d form a generally spiral shape to facilitate formation of a spiral lesion in a wall of the renal artery when the catheter 100 and the resilient members 131a-131d are axially extended beyond the distal tip of the sheath 119.

Figure 11:
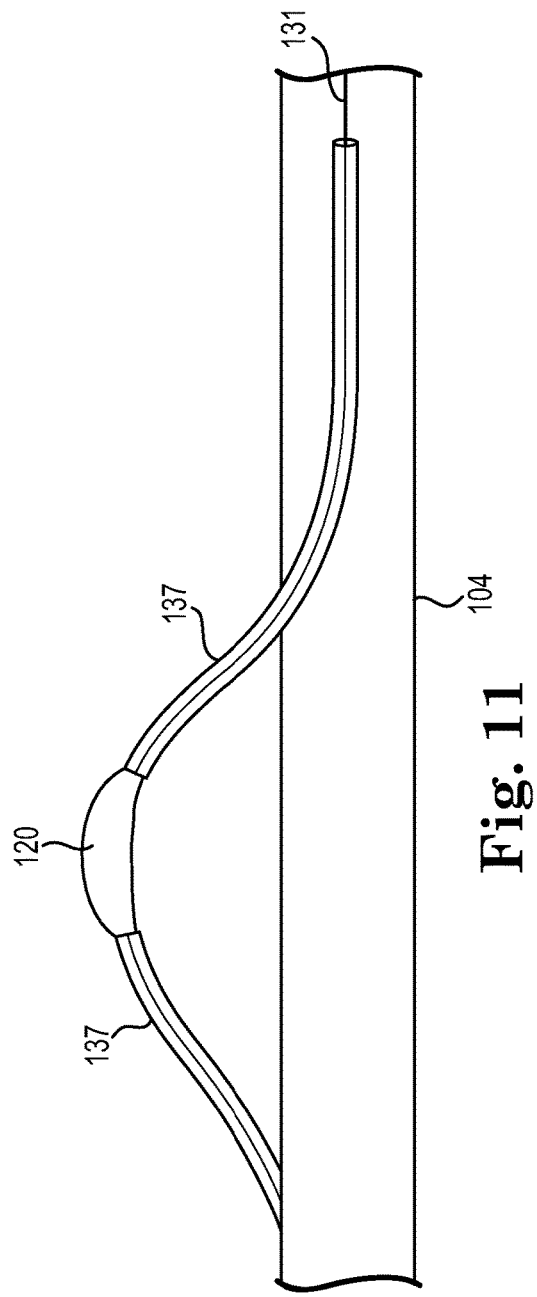
FIG. 11 illustrates a resilient member having an insulating sleeve or coating in accordance with various embodiments.

In some embodiments, the resilient members 131a-131d are mounted structurally independently of one another along the longitudinal length of the distal end of the shaft 104. The shape memories of the resilient members 131a-131d are preferably selected so that the resilient members 131a-131d maintain a spaced-apart relationship when in their expanded deployed configuration. In such configurations, the resilient members 131a-131d need not be covered by an insulating sleeve or coating, although such as sleeve or coating can be included if desired. According to other embodiments that utilize closely spaced resilient members 131a-131d, it may be desirable to cover the resilient members 131a-131d proximal and distal to the electrode(s) 120a-120d with an insulating sleeve or coating. FIG. 11 illustrates a resilient member 131 having an insulating sleeve or coating 137 covering portions of the resilient member 131 proximal and distal to an electrode 120 supported by the resilient member 131.

Figure 12:
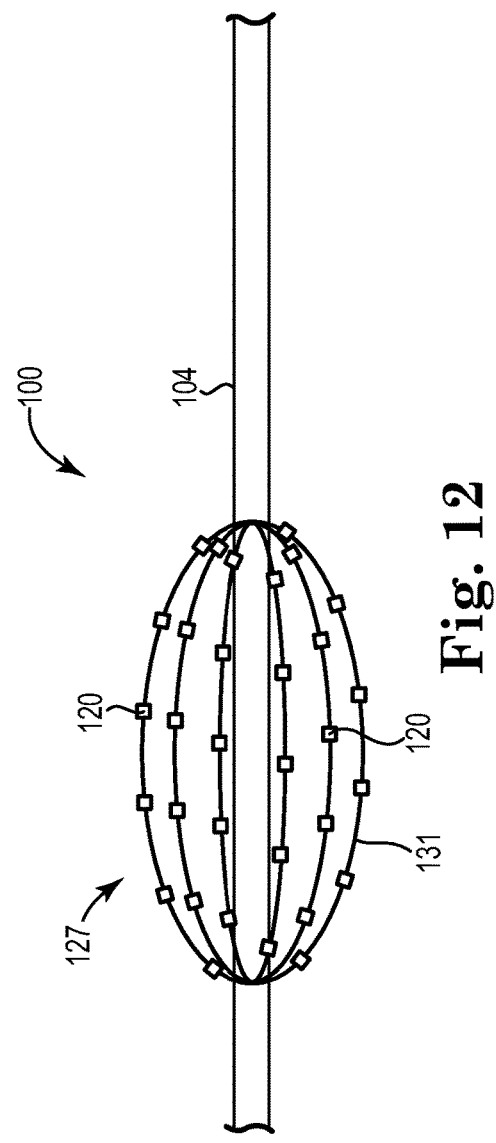
FIGS. 12-15 illustrate various embodiments of an ablation treatment element which includes a multiplicity of resilient members mounted in a structurally cooperative configuration relative to one another.

In accordance with various embodiments, a multiplicity of resilient members 131 are mounted in a structurally cooperative configuration relative to one another along the longitudinal length of the distal end of the shaft 104. Illustrative examples of such embodiments are shown in FIGS. 12-15. FIG. 12, for example, shows a wire segment arrangement 127 formed from a number of resilient members 131 and having a basket or mesh configuration. Each of the resilient members 131 of the basket or mesh has a generally arcuate shape with opposing ends that engage the shaft 104 at common distal and proximal circumferential mounting regions.

Each of the resilient members 131 in FIG. 12 is shown to support a multiplicity of electrodes 120 (e.g., 6 electrodes 120). In some embodiments, the electrodes 120 supported by individual resilient members 131 are connected in series. In other embodiments, all or at least some of the electrodes 120 supported by individual resilient members 131 are connected by way of a separate conductor. In such embodiments, all or at least some of the electrodes 120 supported by individual resilient members 131 are individually controllable, allowing for selective activation and deactivation of electrodes 120 of the basket or mesh arrangements 127.

Figure 15:
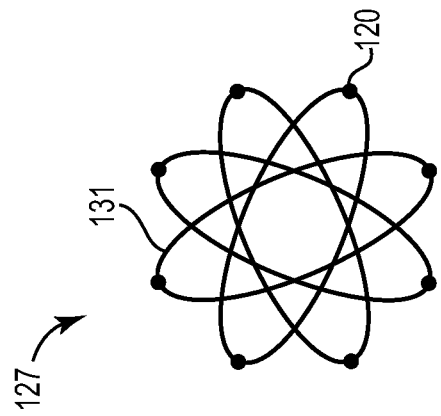
Figure 14:
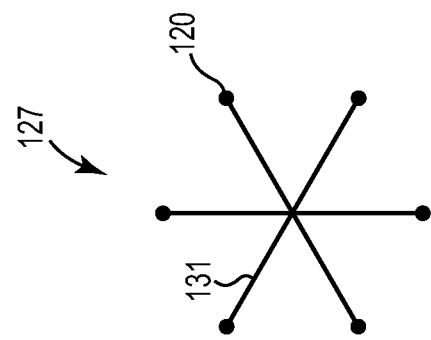
Figure 13:
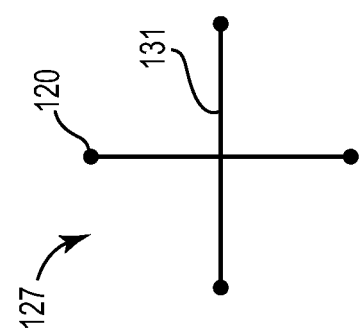

The resilient members 131 of a wire segment arrangement 127 can be arranged to form expandable curves or loops. Illustrative examples of other wire segment arrangement configurations 127 are shown in FIGS. 13-15. These and other wire segment arrangements 127 are contemplated, which may vary in terms of number, circumferential location, and axial location of wire segments and electrodes.

Some or all electrodes 120 of a wire segment arrangement 127 can be energized concurrently, or individual electrodes 120 or subsets of the electrodes 120 can be energized to ablate one or more regions of the perivascular nerves. For example, the electrodes 120 can be individually energizable to produce multiple discrete ablation regions of the renal artery. Selective activation and deactivation of electrodes 120 of one or more resilient members 131 of a wire segment arrangement 127 advantageously provides for formation of lesions having a wide variety of shapes (e.g., spiral, circumferential, spot) and sizes (e.g., such as by increasing or decreasing the number of activated electrodes 120 when creating a lesion). These and other embodiments of the disclosure facilitate formation of lesions in the target vessel having desired shapes and sizes (e.g., a full revolution of a target vessel's wall) without having to reposition the catheter shaft 104 during the ablation procedure.

FIG. 4B illustrates an apparatus for ablating target tissue of a vessel of the body in accordance with various embodiments. In the embodiment shown in FIG. 4B, a catheter 100 includes a multiplicity of elongated resilient members 131 mounted at the distal end of the catheter's shaft 104, and is similar to the catheter embodiment shown in FIG. 4A. Each of the elongated resilient members 131a-131d is mounted along a longitudinal length of the distal end of the shaft 104, engage the shaft 104 at two or more longitudinally spaced-apart locations, and is collapsible when encompassed within the lumen of the sheath 119. When axially extended beyond the distal tip of the sheath 119, the resilient members 131a-131d expand radially outwardly from the shaft 104, causing the electrodes 120a-120d mounted at or near apical locations of the resilient members 131a-131d to move outwardly and into forced engagement with the inner wall of the target vessel.

The embodiment shown in FIG. 4B includes temperature sensors 123 provided at the wire segment arrangement at the distal end of the catheter 100. As is illustrated in FIG. 4B, each of the elongated resilient members 131a-131d supports a temperature sensor 123a-123d, such as a thermocouple, provided at or near an electrode 120a-120d of the elongated resilient members 131a-131d. Each of the temperature sensors 123a-123d is coupled to a respective sensor wire, which extends along the length of the shaft 104 of the catheter 100 and are accessible at the proximal end of the catheter 100.

The sensor wires can be pliable insulated wires that wrap around the resilient members 131 in a barber pole manner. In other configurations, the sensor wires can run parallel, and be bonded, to the resilient members 131a-131d. In further embodiments, the resilient members 131a-131d can be covered with an electrically insulating sleeve or coating, in which case the sensor wires need not have an electrically insulating sleeve or coating.

FIGS. 5 and 6 illustrate a catheter 100 which includes a multiplicity of electrodes supported by a wire segment arrangement in deployed and retracted configurations, respectively, according to various embodiments. FIGS. 5 and 6 illustrate the distal end of a catheter shaft 104 which supports a wire segment arrangement and a retraction mechanism in accordance with low-profile embodiments of the disclosure. In the embodiment shown in FIG. 5, the catheter 100 includes a wire segment arrangement comprising four elongated resilient members 131a-131d that are spaced apart from one another both longitudinally and circumferentially. Each of the four elongated resilient members 131a-131d supports an electrode 120a-120d. The resilient members 131a-131d and electrodes 120a-120d are arranged so that at least one full revolution of a target vessel can be ablated without having to reposition the catheter 100 during the ablation procedure.

The catheter shaft 104 includes lumens through which a pair of control wires 133a, 133b extend. The control wires 133a, 133b can be situated in a common lumen of the shaft 104 or in separate lumens. The distal ends of the control wires 133a, 133b are coupled to proximal ends of the resilient members 131a-131d, which pass into the control wire lumen(s) through a small hole or slit through the shaft wall. A seal arrangement may be positioned within the control wire lumen(s) proximal to the wire segment arrangements to prevent blood from passing into the shaft 104 proximally of the seal arrangement.

In various embodiments, the control wires 133a, 133b are coupled to the resilient members 131a-131d to provide push-pull deployment and retraction of the resilient members 131a-131d by a clinician. In some configurations, the distal ends of the two most distal resilient members 131a and 131b are coupled to control wire 133a, and the distal ends of the two most proximal resilient members 131c and 131d are coupled to control wire 133b. Pushing on the control wire 133a when the resilient members 131a and 131b are in a retracted configuration (see FIG. 6) causes the resilient members 131a and 131b to move outwardly from the shaft 104 into a deployed configuration (see FIG. 5). Pulling on the control wire 133a when the resilient members 131a and 131b are in the deployed configuration causes the resilient members 131a and 131b to move inwardly into the control wire lumen(s) of the shaft 104 (as shown in the retracted configuration of see FIG. 6). Resilient members 131c and 131d can be moved into deployed and retracted configurations by manipulating control wires 133b in the same manner as described above with respect to control wire 133a.

In other embodiments, each of the resilient members 131a-131d is coupled to a single control wire 133. In this configuration, pushing the control wire 133 in a distal direction causes the resilient members 131a-131d to move into the deployed configuration. Pulling the control wire 133 in a proximal direction causes the resilient members 131a-131d to move into the retracted configuration. In further embodiments, each of the resilient members 131a-131d can be coupled to a separate control wire 131. In this configuration, individual resilient members 131a-131d can be moved into the deployed and retracted configurations by pushing and pulling respective control wires 131 coupled to individual resilient members 131a-131d. A sheath (not shown) can be used to cover the wire segment arrangement 131a-131d and electrodes 120a-120d during advancement and extraction of the catheter 100 to and from the target vessel.

Figure 7:
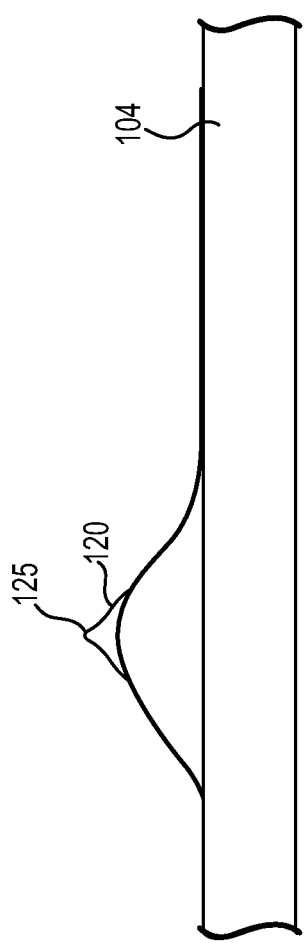
FIGS. 7 and 8 illustrate a catheter which includes a multiplicity of electrodes supported by a wire segment arrangement and having a tissue displacing feature in accordance with various embodiments.
Figure 8:
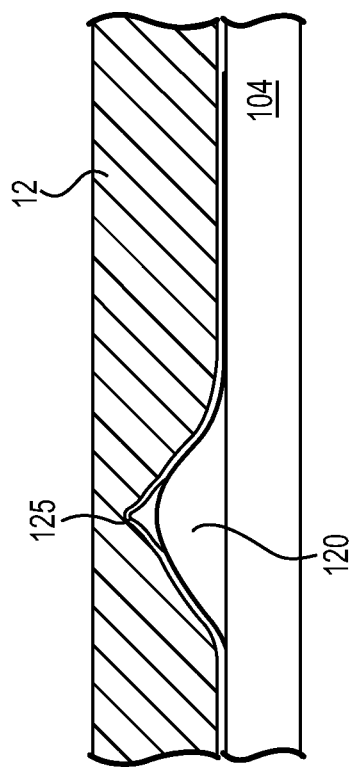

FIGS. 7 and 8 illustrate a catheter 100 which includes a multiplicity of electrodes supported by a wire segment arrangement and having a tissue displacing feature in accordance with various embodiments. For purposes of clarity of explanation, only one wire segment arrangement is shown supporting a single electrode. The electrode shown in FIG. 7 includes a tissue displacing tip 125 that protrudes from the electrode body 120. The length of the tissue displacing tip 125 is selected to limit the displacement depth of the tissue displacing tip 125 into the target vessel wall. For example, and as shown in FIG. 8, the tissue displacing tip 125 of the electrode 120 has a length and radius that allows the tissue displacing tip 125 to forcibly displace tissue of the wall of the renal artery wall 12 to a prescribed depth, but not to pierce through at least the outer wall of the renal artery 12. The tissue displacing electrode 120 and tip 125 for the application shown in FIG. 8 typically has a length no longer than about 2.5 mm.

Configuring the electrode 120 shown in FIGS. 7 and 8 to include a tissue displacing tip 125 effectively decreases the distance between the electrode 120 and the target tissue, such as perivascular renal nerves, by compressing artery tissue between the inner and outer artery walls. Reducing the distance between the electrode 120 and the target tissue advantageously reduces the extent of thermal injury to neighboring non-target tissue and can provide for a reduction in current densities required to ablate perivascular renal nerves.

FIGS. 9 and 10 illustrate arrangements that facilitate controllable expansion and retraction of a wire segment arrangement in accordance with various embodiments. In the embodiment shown in FIG. 9, an elongated resilient member 131 supporting an electrode 120 has a distal end 143 fixedly positioned at an outer wall of the shaft 104. The distal end 143 of the resilient member 131 is preferably bonded or otherwise attached to an inner wall mounting location of the shaft 104 via an access aperture 141. In FIG. 9, the resilient member 131 is shown in an expanded deployed configuration, in which the electrode 120 is supported at a lateral height, $h_1$, relative to the outer wall of the shaft 104. In various embodiments, the lateral height, $h_1$, can range between about 1 mm and about 4.5 mm relative to the outer wall of the shaft 104.

A proximal end of the resilient member 131 is shown to be displaceable in response to proximally and distally directed forces applied to a proximal end of the resilient member 131 or other elongated member that couples to the proximal end of the resilient member 131. The proximal end of the resilient member 131 can be displaced through a travel length, $l_1$, sufficient to limit expansion and collapsing of the resilient member 131 within the lateral height dimension $h_1$, relative to the outer wall of the shaft 104. When in its retracted configuration, the resilient member 131 is compressed against the shaft's outer wall and lies essentially flat along the outer wall of the shaft 104, reducing the lateral height, $h_1$, to a little more than the combined thickness of the electrode 120 and the resilient member 131 (e.g., a combined thickness of about 0.2 mm).

When the resilient member 131 is compressed against the shaft's outer wall, such as when a delivery sheath is advanced over the resilient member 131, the proximal end of the resilient member 131 is forced proximally into its lumen within or along the shaft 104. Advancement of the proximal end of the resilient member 131 into its lumen allows the resilient member 131 to assume a low profile against the exterior wall of the shaft 104. When the delivery sheath is removed, the self-expanding resilient member 131 expands to assume its pre-formed shape, causing the proximal end of the resilient member 131 to move somewhat distally at least partially out of its lumen.

In some configurations, a distally directed force is applied on the proximal end of the resilient member 131 to achieve full expansion of the resilient member 131. In other configurations, elastic forces of the material that forms the resilient member 131 causes self-expansion of the resilient member 131 to its deployed configuration by relaxing tension on the resilient member 131. In various configurations, some degree of distally directed force can be applied on the proximal end of the resilient member 131 to enhance self-expansion of the resilient member 131 to its deployed configuration.

According to some embodiments, a control wire 133 is attached to the distal end of the resilient member 131 and actuatable by a clinician at the proximal end of the catheter 100, such as in the manner described previously with regard to FIGS. 5 and 6. In other embodiments, a control wire 133 is not used, and the retraction and expansion mechanism discussed above operates automatically in response to application and removal of compressive force to and from the resilient member 131 during use.

In the embodiment shown in FIG. 10, a slidable stop arrangement is shown which includes a pair of stops 151a, 151b that capture at least a segment of the resilient member 131. A stop member 153 is mounted to the resilient member 131. The range of axial displacement of the resilient member 131 in the distal direction is limited by contact between the stop member 153 and the distal stop 151a. The range of axial displacement of the resilient member 131 in the proximal direction is limited by contact between the stop member 153 and the proximal stop 151b. The range of axial displacement of the resilient member 131 is therefore limited by the travel distance, $l_2$, defined between a pair of stops 151a, 151b. This travel distance, $l_2$, limits the extent to which the lateral height, $h_2$, of the resilient member 131 can be changed between expanded and collapsed configurations, The travel distance, $l_2$, is preferably selected to allow for full expansion of the resilient member 131 in the deployed configuration, and full compression of the resilient member 131 to achieve a low profile retracted configuration.

When the resilient member 131 (or a control wire coupled to the resilient member 131) is pulled in the proximal direction so that the stop member 153 contacts the proximal stop 151b, the resilient member 131 supporting the electrode collapses toward the outer surface of the shaft 104 until a fully low profile retracted or collapsed configuration is achieved. When tension on the resilient member 131 is released and/or a distally directed force is applied, the stop member 153 advances toward the distal stop 151a, allowing the resilient member 131 to self-expand to its pre-formed deployed shape as the stop member 153 advances toward the distal stop 151a. When the stop member 153 contacts the distal stop 151a, the resilient member 131 achieves its deployed configuration. It is noted that the arrangements shown in FIGS. 9 and 10 can be implemented within a lumen of the shaft 104, within a wall of the shaft 104, or in a side lumen extending at least in part along the outer wall of the shaft 104.

Figure 16:
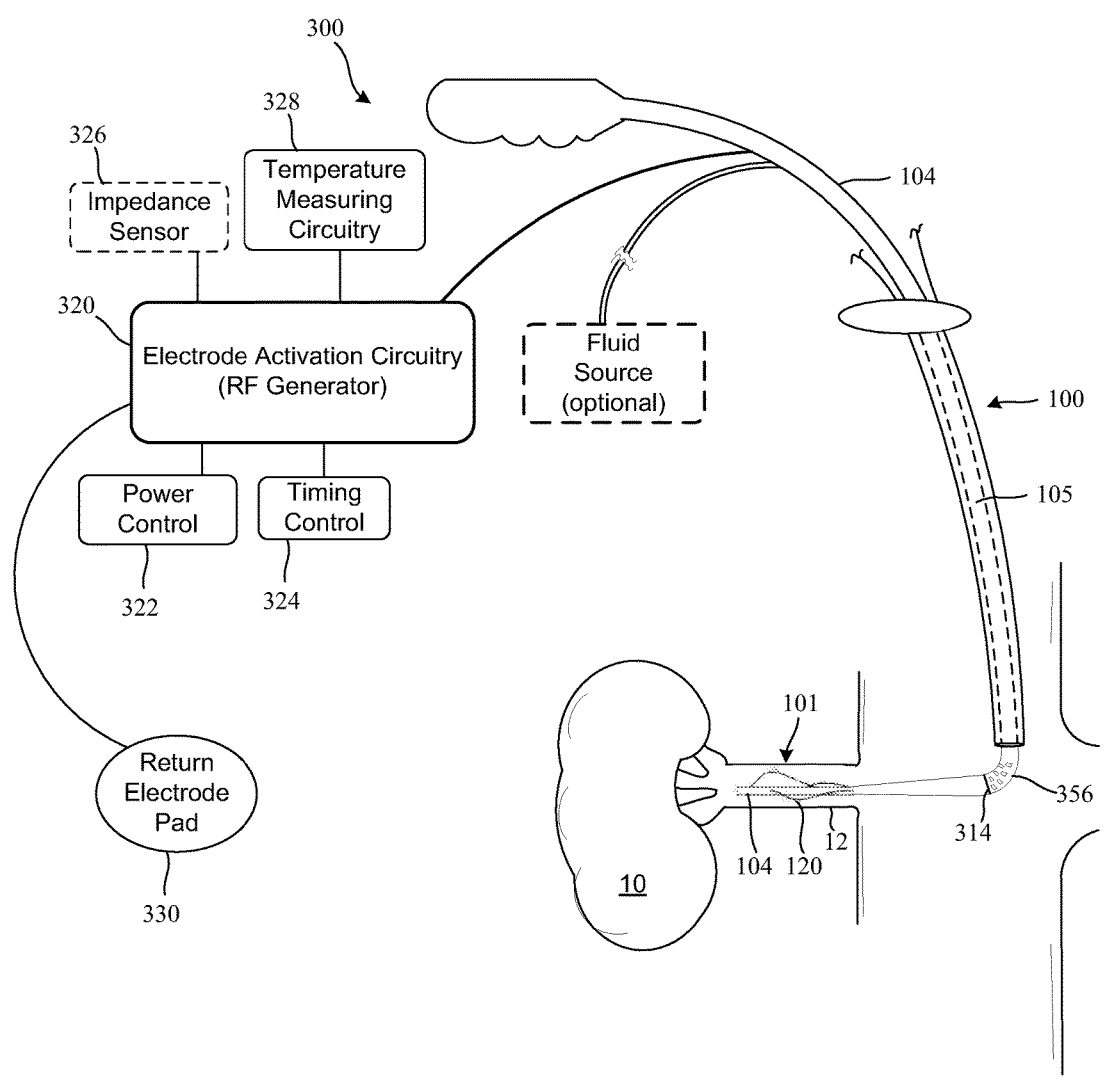
FIG. 16 shows a representative RF renal therapy apparatus in accordance with various embodiments.

FIG. 16 shows a representative RF renal therapy apparatus 300 in accordance with various embodiments of the disclosure. The apparatus 300 illustrated in FIG. 16 includes external electrode activation circuitry 320 which comprises power control circuitry 322 and timing control circuitry 324. The external electrode activation circuitry 320, which includes an RF generator, is coupled to temperature measuring circuitry 328 and may be coupled to an optional impedance sensor 326. The catheter 100 includes a shaft 104 that incorporates a lumen arrangement 105 configured for receiving a variety of components, such as conductors, pharmacological agents, actuator elements, obturators, sensors, or other components as needed or desired.

The RF generator of the external electrode activation circuitry 320 may include a return pad electrode 330 that is configured to comfortably engage the patient's back or other portion of the body near the kidneys. Radiofrequency energy produced by the RF generator is coupled to the treatment element 101 at the distal end of the catheter 101 by the conductor arrangement 110 disposed in the lumen of the catheter's shaft 104.

Renal denervation therapy using the apparatus shown in FIG. 16 is typically performed using the electrodes 120 supported by the wire segment arrangement of the treatment element 101 positioned within the renal artery 12 and the return pad electrode 330 positioned on the patient's back, with the RF generator operating in a monopolar mode. In this implementation, the electrodes 120a-120d, for example, are configured for operation in a unipolar configuration. In other implementations, the electrodes 120 supported by the wire segment arrangement of the treatment element 101 can be configured for operation in a bipolar configuration, in which case the return electrode pad 330 is not needed.

The radiofrequency energy flows through the electrodes 120 in accordance with a predetermined activation sequence (e.g., sequential or concurrent) causing ionic agitation, and therefore friction in the adjacent tissue of the renal artery.

In general, when renal artery tissue temperatures rise above about 113° F. (50° C.), protein is permanently damaged (including those of renal nerve fibers). For example, any mammalian tissue that is heated above about 50° C. for even 1 second is killed. If heated over about 65° C., collagen denatures and tissue shrinks. If heated over about 65° C. and up to 100° C., cell walls break and oil separates from water. Above about 100° C., tissue desiccates.

According to some embodiments, the electrode activation circuitry 320 is configured to control activation and deactivation of the electrodes 120 in accordance with a predetermined energy delivery protocol and in response to signals received from temperature measuring circuitry 328. The electrode activation circuitry 320 controls radiofrequency energy delivered to the electrodes 120 so as to maintain the current densities at a level sufficient to cause heating of the target tissue to at least a temperature of about 55° C.

In some embodiments, temperature sensors are situated at the treatment element 101 and provide for continuous monitoring of renal artery tissue temperatures, and RF generator power is automatically adjusted so that the target temperatures are achieved and maintained. An impedance sensor arrangement 326 may be used to measure and monitor electrical impedance during RF denervation therapy, and the power and timing of the RF generator 320 may be moderated based on the impedance measurements or a combination of impedance and temperature measurements. The size of the ablated area is determined largely by the size, number, and shape of the electrodes 120 supported by the wire segment arrangement of the treatment element 101, the power applied, and the duration of time the energy is applied.

Marker bands 314 can be placed on one or multiple parts of the treatment element 101 to enable visualization during the procedure. Other portions of the catheter 101, such as one or more portions of the shaft 104 (e.g., at the hinge mechanism 356), may include a marker band 314. The marker bands 314 may be solid or split bands of platinum or other radiopaque metal, for example. Radiopaque materials are understood to be materials capable of producing a relatively bright image on a fluoroscopy screen or another imaging technique during a medical procedure. This relatively bright image aids the user in determining specific portions of the catheter 100, such as the tip of the catheter 101, the treatment element 101, and the hinge 356, for example. A braid and/or electrodes of the catheter 100, according to some embodiments, can be radiopaque.

Various embodiments disclosed herein are generally described in the context of ablation of perivascular renal nerves for control of hypertension. It is understood, however, that embodiments of the disclosure have applicability in other contexts, such as performing ablation from within other vessels of the body, including other arteries, veins, and vasculature (e.g., cardiac and urinary vasculature and vessels), and other tissues of the body, including various organs.

It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed is:

1. A method, comprising: introducing a distal end of a flexible catheter shaft to a position within a vessel, the shaft supporting a plurality of elongated resilient members each mounted structurally independent of one another along a longitudinal length of the distal end of the shaft, the resilient members engaging the shaft at a plurality of longitudinally spaced-apart locations; advancing the shaft distal end distally from a sheath surrounding the shaft, such that the members are released from a collapsed position encompassed within the sheath; extending the members radially outward from the shaft at regions between the longitudinally spaced-apart locations, such that one or more electrodes distributed on the resilient members about a perimeter of the catheter shaft engage a wall of the vessel at the regions; supplying energy to the one or more electrodes to form a spiral lesion in the wall of the vessel.

2. The method of claim 1, comprising moving a proximal end of the elongated resilient members relative to the shaft to extend the members radially outward.

3. The method of claim 1, wherein the resilient members are formed of a flexible electrically conductive material that facilitates flexing of the resilient members to accommodate variations in vessel anatomy.

4. The method of claim 1 wherein the resilient members are formed of a flexible material that facilitates expansion and contraction of the resilient members in response to expansion and contraction control forces applied to the resilient members.

5. The method of claim 1, wherein a portion of the resilient members between the electrodes is covered by an electrical insulator.

6. A method, comprising: introducing a distal end of a flexible catheter shaft to a target lumen within a patient relative to an access location, the shaft supporting a plurality of elongated resilient members each mounted structurally independent of one another along a longitudinal length of the distal end of the shaft, the resilient members engaging the shaft at a plurality of longitudinally spaced-apart locations; advancing the shaft distal end distally from a sheath surrounding the shaft, such that the members are released from a collapsed position encompassed within the sheath; extending the members radially outward from the shaft at regions between the longitudinally spaced-apart engagement locations, such that one or more electrodes distributed on the resilient members about a perimeter of the catheter shaft engage a wall of the lumen at the radially extensible regions; supplying energy to the one or more electrodes to form a spiral lesion in the wall of the lumen.

7. The method of claim 6, comprising moving a proximal end of the elongated resilient members relative to the shaft to extend the members radially outward.

8. The method of claim 6, wherein the energy supplied is high frequency AC energy.

9. The method of claim 6, wherein the resilient members are formed of a material that produces elastic forces sufficient to cause self-expansion of the resilient members when axially extended beyond the sheath.

10. The method of claim 6, wherein the electrodes are individually energizable to produce multiple discrete lesions in the spiral along the wall of the lumen.

* * * * *